US011072645B2

(12) United States Patent
Bunk et al.

(10) Patent No.: US 11,072,645 B2
(45) Date of Patent: Jul. 27, 2021

(54) T CELL RECEPTORS WITH IMPROVED PAIRING

(71) Applicant: IMMATICS BIOTECHNOLOGIES GMBH, Tübingen (DE)

(72) Inventors: Sebastian Bunk, Tübingen (DE); Dominik Maurer, Moessingen (DE); Jens Fritsche, Dusslingen (DE); Claudia Wagner, Tübingen (DE); Leonie Alten, Tübingen (DE); Franziska Hoffgaard, Tübingen (DE); Mathias Ferber, Paris (FR)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 498 days.

(21) Appl. No.: 15/833,778

(22) Filed: Dec. 6, 2017

(65) Prior Publication Data

US 2018/0162922 A1    Jun. 14, 2018

Related U.S. Application Data

(60) Provisional application No. 62/497,895, filed on Dec. 8, 2016.

(30) Foreign Application Priority Data

Dec. 8, 2016 (DE) .......................... 102016123893.7

(51) Int. Cl.
| | | |
|---|---|---|
| C07K 14/725 | (2006.01) | |
| C12N 15/09 | (2006.01) | |
| A61K 35/17 | (2015.01) | |
| C12N 5/0783 | (2010.01) | |

(52) U.S. Cl.
CPC .......... *C07K 14/7051* (2013.01); *A61K 35/17* (2013.01); *C12N 5/0638* (2013.01); *C12N 15/09* (2013.01); *C12N 2501/515* (2013.01); *C12N 2510/00* (2013.01)

(58) Field of Classification Search
CPC combination set(s) only.
See application file for complete search history.

(56) References Cited

U.S. PATENT DOCUMENTS

2011/0070208 A1    3/2011   Bertoletti et al.

FOREIGN PATENT DOCUMENTS

| WO | 2011/039507 A1 | 4/2011 |
| WO | 2014/083173 A1 | 6/2014 |
| WO | 2014/153470 A2 | 9/2014 |
| WO | 2016/071343 A1 | 5/2016 |
| WO | 2016146505 A1 | 9/2016 |

OTHER PUBLICATIONS

Janeway et al., Immunobiology, 5th Ed., Garland Science, pp. 106-108, 117-118 and 260-263, 2001.*
Manning et al., Immunity, 1998, 8:413-425.*
Garcia et al., Cell, 2005, 122: 333-336.*
Miles et al, Immunol Cell Biol, 93:433-441, 2015.*
German Search Report of German Patent Application No. 10 2016 123 893.7 dated Jul. 31, 2017.
Zhao, Yangbing et al., "High-Efficiency Transfection of Primary Human and Mouse T Lymphocytes Using RNA Electroporation", Molecular Therapy, Jan. 2006, pp. 151-159, vol. 13, No. 1.
International Search Reporting for PCT/EP2017/081745, dated Apr. 9, 2018.
Database UniProt [Online] May 16, 2012, XP055460088, retrieved from the Internet: http://ibis/exam/dbfetch.jsp?id=UNIPROT:H9KWC7.
C. Govers et al. "T cell receptor gene therapy: strategies for optimizing transgenic TCR pairing", Trends in Molecular Medicine, Elsevier Current Trends. vol. 16(2): 77-87. Feb. 1, 2010. XP026904285. DOI: 10.1016/J.MOLMED.2009.12.004.
Thomas Hoffmann et al. "Quantitative Analysis of the Association Angle Between T-cell Receptor V[alpha]/V[beta] Domains Reveals important features for Epitope Recognition." Plos Computational Biology. vol. 11(7). p. e1004244. Jul. 17, 2015. DOI: 10.1371/journal.pcbi.1004244.
Preeti Sharma et al. "Subtle changes at the variable domain interface of the T-cell receptor can strongly increase affinity." Journal of Biological Chemistry. vol. 293(5): 1820-1834. Dec. 11, 2017. DOI: 10.1074/jbc.M117.814152.
Spear TT et al. "TCR modifications that enhance chain pairing in gene-modified T cells can augment cross-reactivity and alleviate CD8 dependence." Journal of Leukocyte Biology, Federation of American Societies for Experimental Biology. vol. Early View (Version of Record online). Jan. 19, 2018. DOI: 10.1002/JLB.5A0817-314R.
Search Report for DE 10 2016 123 893.7 dated Jul. 25, 2017.
Z. Yangbing. High efficiency transfection of primary human and mouse T lymphocytes using RNA electroporation. 2006. In: Mol. Ther., vol. 13, S. 151-159.
Yang, et al., "Structural Basis for Clonal Diversity of the Public T Cell Response to a Dominant Human Cytomegalovirus Epitope," Journal of Biological Chemistry, (2015), vol. 290, No. 48: 29106-29119.
"T cell receptor alpha chain, partial [Callithrix jacchus]", (2016), [BAJ06711], [Jul. 25, 2016], Retrieved from GenBank, [online], Accession No. BAJ06711, [Retrieved on Apr. 15, 2021].
"SubName: Full=Uncharacterized protein {ECO:0000313|Ensembl:ENSCJAP00000012641)," (2016), [Sep. 7, 2016] retrieved from UniProtKB/TrEMBL [retrieved on Apr. 15, 2021.], accession No. H9KINC7.

\* cited by examiner

*Primary Examiner* — Mark Halvorson
(74) *Attorney, Agent, or Firm* — McBee Moore & Vanik IP, LLC

(57) ABSTRACT

The present invention relates to modified T cell receptor (TCR) α or β chains, or heterodimers comprising the same, wherein in the variable domain of said modified α or β chain, an amino acid at position 44 according to the IMGT numbering is substituted by another suitable amino acid in order to improve pairing of desired chains.

5 Claims, 11 Drawing Sheets

Specification includes a Sequence Listing.

|  |  |  | TRBV: human TRBV6-5 |  |  | TRAV: human TRAV8-6 |  |  |
|---|---|---|---|---|---|---|---|---|
| FR1-IMGT | 1 | 1 | aat | ASN | N | 1 | 0 | agc | ALA | A |
|  | 2 | 2 | gct | ALA | A | 2 | 1 | cag | GLN | Q |
|  | 3 | 3 | ggt | GLY | G | 3 | 2 | tct | SER | S |
|  | 4 | 4 | gtc | VAL | V | 4 | 3 | gtg | VAL | V |
|  | 5 | 5 | act | THR | T | 5 | 4 | acc | THR | T |
|  | 6 | 6 | cag | GLN | Q | 6 | 5 | cag | GLN | Q |
|  | 7 | 7 | acc | THR | T | 7 | 6 | ctt | LEU | L |
|  | 8 | 8 | cca | PRO | P | 8 | 7 | gac | ASP | D |
|  | 9 | 9 | aaa | LYS | K | 9 | 8 | agc | SER | S |
|  | 10 | 10 | ttc | PHE | F | 10 | 9 | caa | GLN | Q |
|  | 11 | 11 | cag | GLN | Q | 11 | 10 | gtc | VAL | V |
|  | 12 | 12 | gtc | VAL | V | 12 | 11 | cct | PRO | P |
|  | 13 | 13 | ctg | LEU | L | 13 | 12 | gtc | VAL | V |
|  | 14 | 14 | aag | LYS | K | 14 | 13 | ttt | PHE | F |
|  | 15 | 15 | aca | THR | T | 15 | 14 | gaa | GLU | E |
|  | 16 | 16 | gga | GLY | G | 16 | 15 | gaa | GLU | E |
|  | 17 | 17 | cag | GLN | Q | 17 | 16 | gcc | ALA | A |
|  | 18 | 18 | agc | SER | S | 18 | 17 | cct | PRO | P |
|  | 19 | 19 | atg | MET | M | 19 | 18 | gtg | VAL | V |
|  | 20 | 20 | aca | THR | T | 20 | 19 | gag | GLU | E |
|  | 21 | 21 | ctg | LEU | L | 21 | 20 | ctg | LEU | L |
|  | 22 | 22 | cag | GLN | Q | 22 | 21 | agg | ARG | R |
|  | 23 | 23 | tgt | CYS | C | 23 | 22 | tgc | CYS | C |
|  | 24 | 24 | gcc | ALA | A | 24 | 23 | aac | ASN | N |
|  | 25 | 25 | cag | GLN | Q | 25 | 24 | tac | TYR | Y |
|  | 26 | 26 | gat | ASP | D | 26 | 25 | tca | SER | S |
| CDR1-IMGT | 27 | 27 | atg | MET | M | 27 | 26 | tcg | SER | S |
|  | 28 | 28 | aac | ASN | N | 28 | 27 | tct | SER | S |
|  | 29 | 29 | cat | HIS | H | 29 | 28 | gtt | VAL | V |
|  | 30 | 30 | gaa | GLU | E | 30 | 29 | tca | SER | S |
|  | 31 | *31 | tac | TYR | Y | 31 | 30 | gtg | VAL | V |
|  | 32 | * | ... | ... | ... | 32 | *31 | tat | TYR | Y |
|  | 33 |  | — | — | — | 33 | * | — | — | — |
|  | 34 |  | — | — | — | 34 | * | — | — | — |
|  | 35 |  | — | — | — | 35 |  | — | — | — |
|  | 36 |  | — | — | — | 36 |  | — | — | — |
|  | 37 |  | — | — | — | 37 |  | — | — | — |
|  | 38 |  | — | — | — | 38 |  | — | — | — |

Fig. 1A

|  | TRBV: human TRBV6-5 | | | | | TRAV: human TRAV8-6 | | | | |
|---|---|---|---|---|---|---|---|---|---|---|
| FR2-IMGT | 39 | 32 | atg | MET | M | 39 | 32 | ctc | LEU | L |
|  | 40 | 33 | tcc | SER | S | 40 | 33 | ttc | PHE | F |
|  | 41 | 34 | tgg | TRP | W | 41 | 34 | tgg | TRP | W |
|  | 42 | 35 | tat | TYR | Y | 42 | 35 | tat | TYR | Y |
|  | 43 | 36 | cga | ARG | R | 43 | 36 | gtg | VAL | V |
|  | 44 | 37 | caa | GLN | Q | 44 | 37 | caa | GLN | Q |
|  | 45 | 38 | gac | ASP | D | 45 | 38 | tac | TYR | Y |
|  | 46 | 39 | cca | PRO | P | 46 | 39 | ccc | PRO | P |
|  | 47 | 40 | ggc | GLY | G | 47 | 40 | aac | ASN | N |
|  | 48 | 41 | atg | MET | M | 48 | 41 | caa | GLN | Q |
|  | 49 | 42 | ggg | GLY | G | 49 | 42 | gga | GLY | G |
|  | 50 | 43 | ctg | LEU | L | 50 | 43 | ctc | LEU | L |
|  | 51 | 44 | agg | ARG | R | 51 | 44 | cag | GLN | Q |
|  | 52 | 45 | ctg | LEU | L | 52 | 45 | ctt | LEU | L |
|  | 53 | 46 | att | ILE | I | 53 | 46 | ctc | LEU | L |
|  | 54 | 47 | cat | HIS | H | 54 | 47 | ctg | LEU | L |
|  | 55 | 48 | tac | TYR | Y | 55 | 48 | aag | LYS | K |
| CDR2-IMGT | 56 | 49 | tca | SER | S | 56 | *49 | tat | TYR | Y |
|  | 57 | 50 | gtt | VAL | V | 57 | *50 | tta | LEU | L |
|  | 58 | 51 | ggt | GLY | G | 58 | *51 | tca | SER | S |
|  | 59 | 52 | gct | ALA | A | 59 | *52 | gga | GLY | G |
|  | 60 | 53 | ggt | GLY | G | 60 |  |  |  |  |
|  | 61 | 54 | atc | ILE | I | 61 |  |  |  |  |
|  | 62 |  |  |  |  | 62 |  |  |  |  |
|  | 63 |  |  |  |  | 63 |  |  |  |  |
|  | 64 |  |  |  |  | 64 |  |  |  |  |
|  | 65 |  |  |  |  | 65 |  |  |  |  |
| FR3-IMGT | 66 | 55 | act | THR | T | 66 | *53 | tcc | SER | S |
|  | 67 | 56 | gac | ASP | D | 67 | *54 | acc | THR | T |
|  | 68 | 57 | caa | GLN | Q | 68 | *55 | ctg | LEU | L |
|  | 69 | 58 | gga | GLY | G | 69 | *56 | gtt | VAL | V |
|  | 70 | 59 | gaa | GLU | E | 70 | *57 | gaa | GLU | E |
|  | 71 | 60 | gtc | VAL | V | 71 | *58 | agc | SER | S |
|  | 72 | 61 | ccc | PRO | P | 72 | *59 | atc | ILE | I |
|  | 73 | *62 | — | — | — | 73 | * | — | — | — |
|  | 74 | *63 | aat | ASN | N | 74 | *60 | aac | ASN | N |
|  | 75 | *64 | ggc | GLY | G | 75 | 61 | ggt | GLY | G |
|  | 76 | 65 | tac | TYR | Y | 76 | 62 | ttt | PHE | F |
|  | 77 | 66 | aat | ASN | N | 77 | 63 | gag | GLU | E |

Fig. 1B

|  | TRBV: human TRBV6-5 | | | | TRAV: human TRAV8-6 | | | |
| --- | --- | --- | --- | --- | --- | --- | --- | --- |
|  | 78 | 67 | gtc | VAL | V | 78 | 64 | gct | ALA | A |
|  | 79 | 68 | tcc | SER | S | 79 | 65 | gaa | GLU | E |
|  | 80 | 69 | aga | ARG | R | 80 | 66 | ttt | PHE | F |
|  | 81 | 70 | tca | SER | S | 81 | 67 | aac | ASN | N |
|  | 82 |  | -- | -- | -- | 82 | 68 | aag | LYS | K |
|  | 83 | 71 | acc | THR | T | 83 | 69 | agt | SER | S |
|  | 84 | 72 | aca | THR | T | 84 | 70 | caa | GLN | Q |
|  | 85 | 73 | gag | GLU | E | 85 | 71 | act | THR | T |
|  | 86 | 74 | gat | ASP | D | 86 | 72 | tcc | SER | S |
|  | 87 | 75 | ttc | PHE | F | 87 | 73 | ttc | PHE | F |
|  | 88 | 76 | ccg | PRO | P | 88 | 74 | cac | HIS | H |
|  | 89 | 77 | ctc | LEU | L | 89 | 75 | ttg | LEU | L |
|  | 90 | 78 | agg | ARG | R | 90 | 76 | agg | ARG | R |
|  | 91 | 79 | ctg | LEU | L | 91 | 77 | aaa | LYS | K |
|  | 92 | 80 | ctg | LEU | L | 92 | 78 | ccc | PRO | P |
|  | 93 | 81 | tcg | SER | S | 93 | 79 | tca | SER | S |
|  | 94 | 82 | gct | ALA | A | 94 | 80 | gtc | VAL | V |
|  | 95 | 83 | gct | ALA | A | 95 | 81 | cat | HIS | H |
|  | 96 | 84 | ccc | PRO | P | 96 | 82 | ata | ILE | I |
|  | 97 | 85 | tcc | SER | S | 97 | 83 | agc | SER | S |
|  | 98 | 86 | cag | GLN | Q | 98 | 84 | gac | ASP | D |
|  | 99 | 87 | aca | THR | T | 99 | 85 | acg | THR | T |
|  | 100 | 88 | tct | SER | S | 100 | 86 | gct | ALA | A |
|  | 101 | 89 | gtg | VAL | V | 101 | 87 | gag | GLU | E |
|  | 102 | 90 | tac | TYR | Y | 102 | 88 | tac | TYR | Y |
|  | 103 | 91 | ttc | PHE | F | 103 | 89 | ttc | PHE | F |
|  | 104 | 92 | tgt | CYS | C | 104 | 90 | tgt | CYS | C |
| CDR3-IMGT | 105 | 93 | gcc | ALA | A | 105 | 91 | gct | ALA | A |
|  | 106 | 94 | agc | SER | S | 106 | 92 | gtg | VAL | V |
|  | 107 | 95 | agt | SER | S | 107 | 93 | agt | SER | S |
|  | 108 | 96 | tat | TYR | Y |  |  |  |  |  |
|  | 109 | 97 | -- | -- | -- |  |  |  |  |  |

Fig. 1C

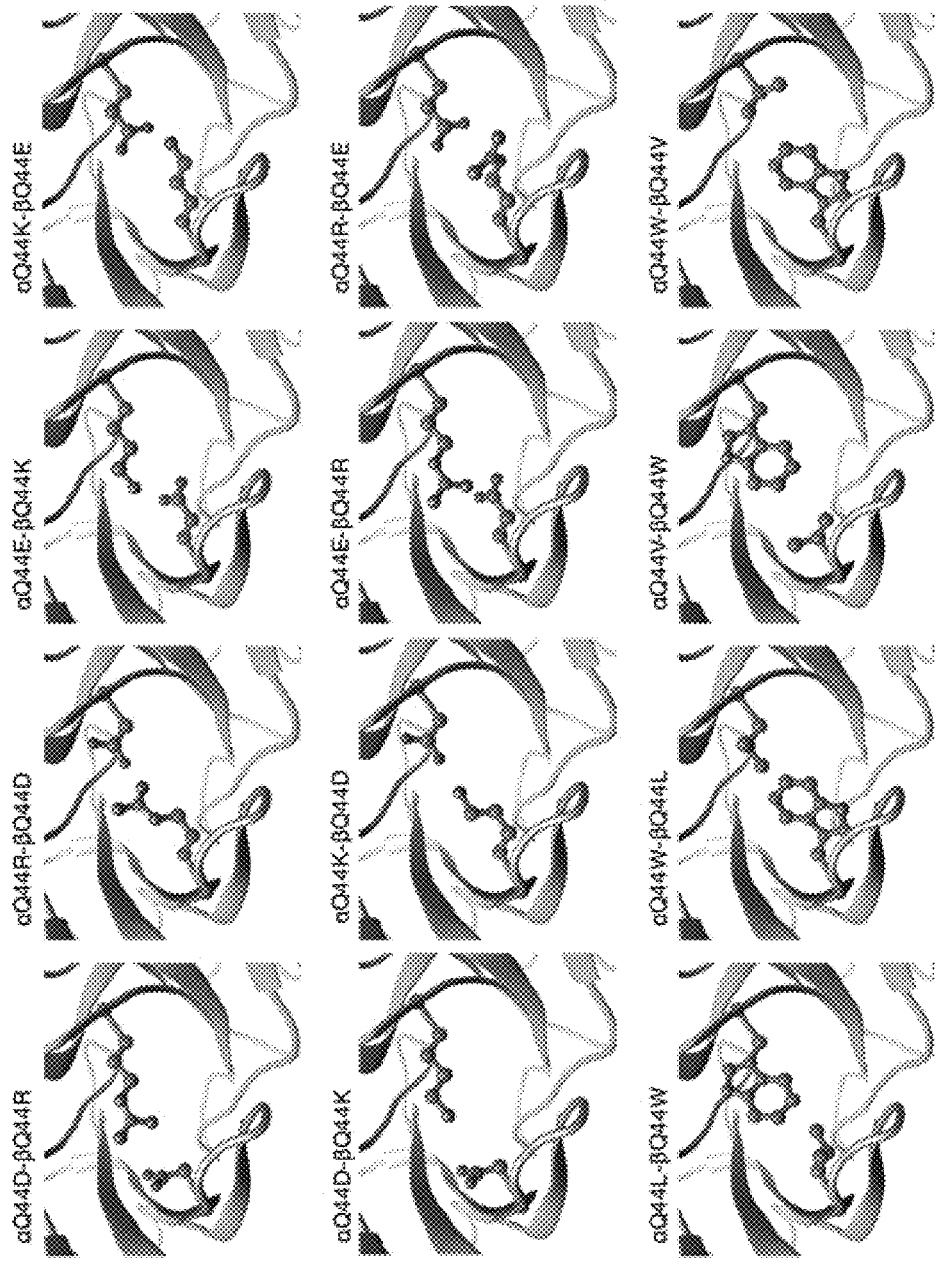
Fig. 2A
Fig. 2B

SEQ ID NO 1: TCR alpha chain variable domain of R7P1D5 (TRAV5)

```
     FR1        CDR1              FR2        CDR2
GEDVEQS LFLSVREGDSSVINCTYT DSSSTY    LY WYKQ EPGAGLQLLTY IFS      60
    NMDMKQD QRLTVLLNKKDHLSLRIADTQTGDSAIYF CAE   106
           FR3                CDR3
```

SEQ ID NO 2: TCR beta chain variable domain of R7P1D5 (TRBV12-4)

```
DAGVIQSPRHEVTEMGQEVTLRCKPI SGHDY      LF WYRQ TMMRGLELLIY FNNNV    60
R    IDDSGMPEDRFSAKMP NASFSTLKIQPSEPRDSAVY FCAS   106
```

SEQ ID NO 3: TCR alpha chain variable domain of TRAV 8-6

```
AQSVTQLDSQVPVFEEAPVELRCNY SSSVSVY     LF WYVQ YPNQGLQLLLK YLSG    60
     STLVESI NGFEAEFNKSQTSFHLRKPSVHISDTAEYFC AVS    107
```

SEQ ID NO 4: TCR beta chain variable domain of TRBV 6-5

```
NAGVTQTPKFQVLKTGQSMTLQCAQD MNHEY      MS WYRQ DPGMGLRLIHY SVGAG   60
I    TDQGEVP NGYNVSRS TTEDFPLRLLSAAPSQTSVYFC ASSY    108
```

Fig. 3

T CELL RECEPTORS WITH IMPROVED PAIRING

CROSS-REFERENCE TO RELATED APPLICATIONS

This application claims priority to U.S. Provisional Application No. 62/497,895, filed 8 Dec. 2016 and German Patent Application No. 10 2016 123 893.7, filed 8 Dec. 2016. The disclosures of the priority applications are incorporated in their entirety herein by reference.

This application is also related to PCT/EP2017/081745 filed 6 Dec. 2017, the content of which is incorporated herein by reference in its entirety.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-082001_ST25.txt" created on 26 Mar. 2020, and 6,214 bytes in size) is submitted concurrently with the instant application, and the entire contents of the Sequence Listing are incorporated herein by reference.

BACKGROUND

Field of the Invention

The present invention relates to modified T cell receptor (TCR) α or β chains, or heterodimers comprising the same, wherein in the variable domain of said modified α or β chain, an amino acid at position 44 according to the IMGT numbering is substituted with another suitable amino acid, in order to improve pairing of desired chains.

Description of Related Art

The adaptive immune system consists of antibodies, B cells, and CD4$^+$ and CD8$^+$ T cells. These enable a highly specific response against a particular immunogenic target. T cell receptors (TCRs) are disulfide-linked membrane-anchored heterodimeric proteins that normally consist of the highly variable alpha (α) and beta (β) chains expressed as part of a complex with the invariant CD3 chain molecules on the surface of T cells. An important step in the process of forming the TCR heterodimer is called "pairing". T cells expressing paired receptors are referred to as α:β (or αβ) T cells, although a minority of T cells express an alternate receptor, formed by variable gamma (γ) and delta (δ) chains, referred to as γδ T cells.

TCRs are located on the surface of T cells, and as antigen receptor molecules are responsible for the recognition of suitably processed antigen presented to T cells by major histocompatibility complex (MHC) molecules on the surface of antigen-presenting cells (APCs), leading potentially to the activation of the T cell and an immune response to the antigen.

Each chain of the TCR is composed of two extracellular domains: A variable (V) region and a constant (C) region, both belonging to the immunoglobulin superfamily (IgSF) domain forming antiparallel β-sheets. The constant region is proximal to the cell membrane, followed by a transmembrane region and a short cytoplasmic tail, while the variable region binds to the peptide/MHC complex of an antigen presenting cell.

The variable domains of both the TCR α-chain and β-chain each have three hypervariable or complementarity determining regions (CDRs), which form the antigen binding site. The variable region of the β-chain has an additional area of so-called hypervariability (HV4) that does not normally contact antigen and, therefore, is not considered a CDR. Importantly, CDRs 1 and 2 of both chains are germline encoded while CDR3 α and β are largely non-template encoded but produced by somatic recombination (Davis & Bjorkman 1988) In humans, the diversity of TCR molecules is achieved by the αβ pairing of a set composed 47 Vα and 54 Vβ sequences that are combined to achieve the final diversity of CDR3 lengths and sequences.

CDR3 are the main CDRs responsible for recognizing said processed antigen, although CDR1 of the α-chain has also been shown to interact with the N-terminal part of the antigenic peptide (Cole et al. 2009), whereas CDR1 of the β-chain only interacts occasionally with the C-terminal part of the peptide.

CDR2 is thought to mostly recognize the MHC. The HV4 region of the β-chain is not thought to participate in antigen recognition, but has been shown to interact with so-called superantigens (Li et al. 1998). Despite the commonly accepted paradigm of CDR1 and CDR2 binding mostly to the MHC and CDR3 to the antigenic peptide, some studies have revealed the true complexity of antigen recognition by the TCR, by showing that all CDRs regions can occasionally interact both with the antigen and the MHC (Burrows et al. 2010, Roomp et al. 2011).

The adoptive transfer approach was developed to use a mechanism for cancer therapy (Rosenberg et al. 1988), whereby T cells transduced with the genes encoding for the α and β chains of a tumor-specific T cell receptor (TCR) mediate anti-tumor immunity in patients. In recent years, this approach has been the center of a lot of attention. As one strategy, TCR gene therapy provides patients with autologous T cells that are thus genetically engineered with transgenic TCR chains. This technique provides a promising approach for the treatment of cancer and tumors. For doing so, TCR alpha and beta chains detecting/binding a specific antigen-MHC complex are cloned into a wildtype T cell taken from a patient. The transgenic T cell is then proliferated in vitro, and the proliferated cells are given back to the patient, in order to provide an immune response against e.g. the tumor.

In effect, the transgene T cells thus produced both expresses a wildtype TCR having wildtype alpha and beta chains, and the transgenic TCR with the alpha and beta chains specific for the respective recombinant antigen-MHC complex. Both the wildtype alpha and beta chains and the transgenic alpha and beta chains are usually still capable of cross-pairing with each other (Shao et al. 2010). This undesired possibility is called "TCR mispairing", and is a recognized problem in the field of TCR (gene) therapy.

The mispairing and the incorrect pairing between a transgenic TCR α or β chain and an endogenous TCR β or α chain, respectively, results in a reduced surface expression of the transgenic TCRαβ heterodimer, which in turn reduces the functional avidity of the modified T cells. Furthermore, T cells expressing mispaired TCRs and expanded under high IL-2 conditions were demonstrated to induce graft—versus—host disease (GvHD) in a preclinical model (Bendle et al, 2009).

Some strategies for the optimization of transgenic TCR α and β pairing in order to enhance the functional avidity of therapeutic T cells have been discussed, e.g., in Govers et al. (2010).

Among these possibilities to avoid mispairing are the following:

1. Murinized TCRs: In this approach, human TCRα and β constant chains are replaced by the corresponding murine domains. Although human and murine TCR-C domains show a high degree of homology, small differences affect the stability of TCR/CD3 interactions and hence TCR surface expression levels.

2. Cysteine-modified TCRs: This approach introduces cysteine amino acids at a structurally favorable position, and hence allows the formation of an additional disulfide bridge and promotes correct pairing between the two TCR chains. Site-directed mutations of e.g. T480 in the TCR alpha constant chain and S57C in the TCR beta constant chain resulted in a TCR heterodimer linked by two interchain bonds (i.e., an introduced disulfide bridge plus an endogenous transmembrane disulfide bridge (position No. 95 in the alpha constant domain and position No. 131 in the beta constant domain).

3. Domain swapping: Constant domains are swapped between the α and β chains of a tumor-specific T cell receptor, creating a domain-swapped (ds) TCR. When correctly paired, these dsTCR chains retain all domains necessary to recruit CD3 proteins, to express on the T cell surface, and to mediate functional T cell responses upon engaging a target antigen. By contrast, mispaired TCRs containing one dsTCR chain and one wild-type TCR chain lack key domains necessary for CD3 recruitment, export, and signaling, and thus are unable to mediate deleterious autoimmunity.

4. Exclusive TCR heterodimers: In this approach, sterical and electrostatic forces are exploited to facilitate correct pairing between TCR alpha and beta transgenes and at the same time inhibit pairing between exogenous and endogenous TCR alpha and beta chains. One example uses site-directed mutations to introduce an S85R into the alpha constant domain and R88G in the beta constant domain, in order to obtain the required changes in electrostatic charges, and hence generate a reciprocal 'knob-into-hole' configuration, which allegedly minimally distorts secondary and tertiary structures.

5. The use of chimeric TCR-CD3ζ chain having each TCR chain fused to a CD3 molecule.

6. The use of single-chain TCRs wherein the Vα of a defined TCR is fused to the beta chain using a flexible peptide linker.

7. The use of shRNA sequences or zinc finger nucleases to knock down the expression of the endogenous TCR.

Another approach was proposed by O'Shea et al. (1993) who designed a pair of peptides, termed "velcro", that were able to pair with one another due to favorable electrostatic interactions in the heterodimeric state. The authors demonstrated that the two peptides are predominantly unfolded in isolated form but associate preferentially to form a stable parallel, coiled coil heterodimer when mixed. This approach was also applied by Chang et al. (1994) in order to produce soluble TCR in which heterodimeric complex was favored by fusing the peptides to truncated alpha and beta chains respectively.

WO 2014/153470 A2 discloses methods and compositions for modifying TCR genes, using nucleases (zinc finger nucleases or TAL nucleases) to modify TCR genes by targeted disruption.

WO 2014/083173 relates to a method for the production of novel T cell receptors which provide a reduced risk of adverse events in immune therapy, specifically in adoptive T cell transfer.

WO 2016/071343 A1 relates to modified T cell receptors (TCRs) and to their use in adoptive cell therapy (ACT), in particular for the transfer of T lymphocytes. The TCRs are mutated in the transmembrane regions of the alpha and beta chains with mutations favoring the correct TCR chain pairing.

Although promising, several hurdles, including the proper expression of the exogenous TCR, have hampered the clinical impact of the above approaches. Insufficient clinical responses indicate that many problems are still to be solved. As T cell functional avidity is dictated mainly by both TCR affinity and the number of TCR molecules expressed, much efforts have been devoted to improving these biophysical properties in TCR-engineered cells using two important approaches: (a) the improvement of TCR affinity and (b) the enhancement of TCR expression. To improve TCR affinity, attempts have been made to select high affinity receptors or to enhance the affinity of the transferred receptor by point mutations. Alternatively, various approaches have been devised to increase the number of TCRs on the surface of transduced cells. These include engineering expression vectors, using of co don-optimized TCR sequences, eliminating glycosylation sites and improving pairing of the introduced TCR chains.

SUMMARY

There is therefore still the need to provide approaches in order to effectively avoid TCR mispairing. These further approaches should be easy to introduce, and efficiently reduce the occurrence of mispaired TCR heterodimers, while increasing the abundance of correctly paired TCR heterodimers, i.e., pairs of transgenic alpha and beta chains in respectively modified T cells. Also, a methodology requiring minimal manipulation of TCR chains and host T cells would be desirable.

These and further objects are solved by methods and means according to the present invention.

According to the first aspect of the present invention, a modified T cell receptor (TCR) α or β chain, or a fragment or derivative thereof is provided that maintains the ability to bind to an antigen-MHC complex, wherein, in the variable domain of said modified α or β chain, a Q or any other amino acid at position 44 according to the IMGT numbering is substituted with another suitable amino acid. Suitable amino acids, as is shown also in the following, maintain the pairing specificity of the TCR α and β chains as modified, while reducing the pairing with an undesired α or β chain, e.g. a non-modified chain.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A, 1B, 1C, 2A, 2B, and 3-8 depict embodiments of the disclosure as disclosed herein.

DETAILED DESCRIPTION OF A PREFERRED EMBODIMENT

Figure 4A:
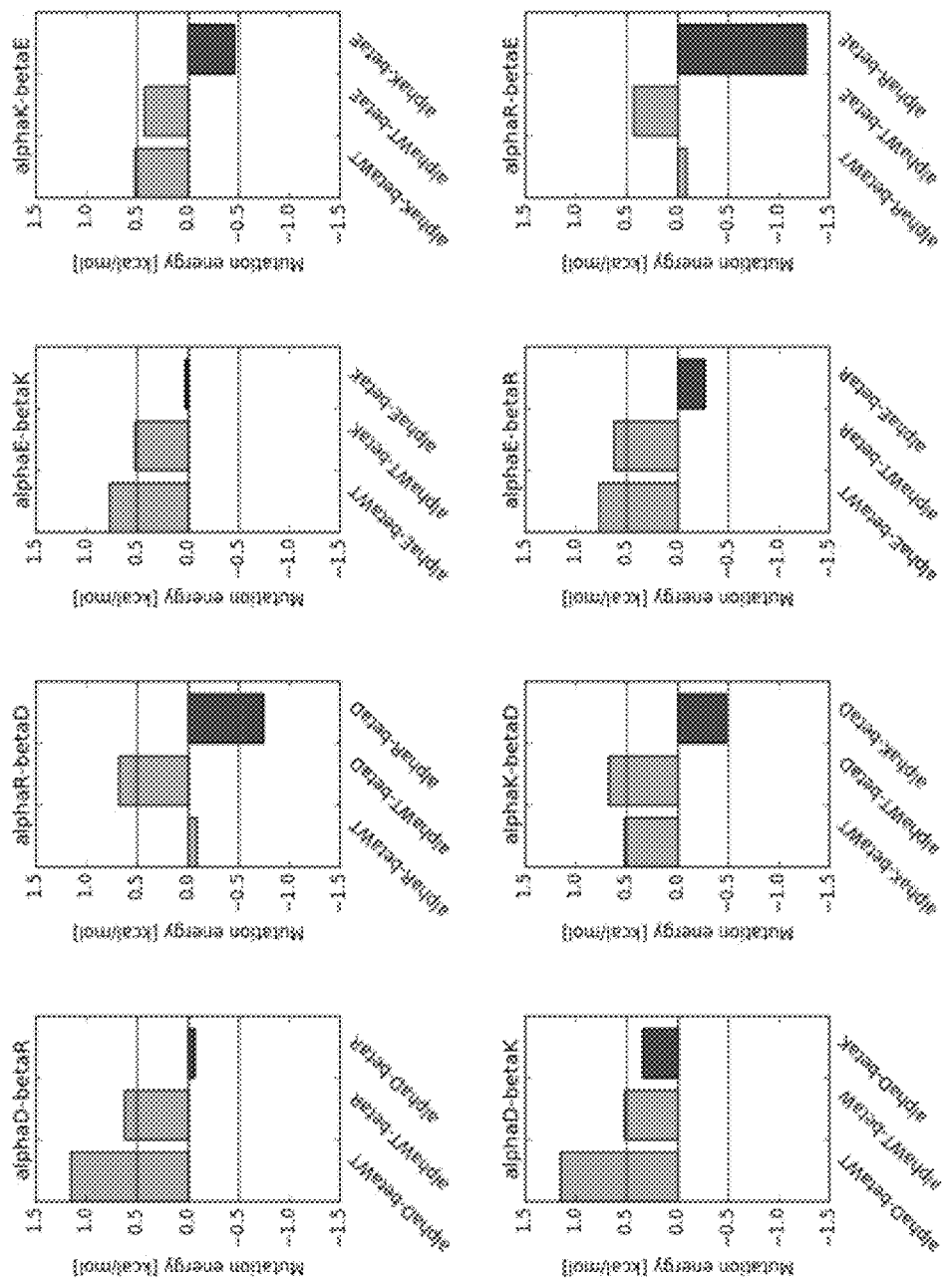

Because it is located in the FR2 region, position 44 is known to not be directly in contact with the target of the TCR binding site. It is therefore assumed that a substitution at position 44 would not be crucial for and/or interfere with a specific target epitope recognition.

Amino acids according to the invention can be selected from the 20 α-amino acids as used in living organisms (L-amino acids). "Suitable" amino acids shall include both these amino acids (i.e. the 20 α-amino acids as used in living organisms, and L-amino acids), as well as "unusual" amino acids (e.g. β-amino acids, or D-amino acids) or modified amino acids. Preferred are the 20 α-amino acids as used in living organisms.

The numbering of the amino acid residues in the TCR α chain and β chain is according to the IMGT standard, as disclosed in Lefranc et al. (2001). The IMGT standard is a universal system of rules to assign unambiguous numbers to amino acid residues in immunoglobulin molecules, including TCR α and β variable chains. See FIGS. 1 A to C for a comparison of the IMGT numbering (bold) to the Kabat numbering. In FIG. 1B, Q44 in the α chain (TRAV) and β chain (TRBV) are marked in gray. The numbering according to the IMGT standard may deviate from the naïve numbering of a given amino acid sequence of a TCR variable domain, in particular due to blanks in the CDR sequences, as can be seen in FIG. 1 A-C.

Q44 according to the IMGT numbering is a highly conserved residue in the Framework 2 (FR2) region, and is shared by almost all TCR α chains, except of TRAV2, TRAV24, TRAV29/DV5 and TRAV40, and is shared by all TCR β genes, except of TRBV14 (Lefranc et al, 2001, Strong et al., 1999). Furthermore, Q44 is very often part of a 4 AA motif comprising WYXQ, with X being, for example, R, V, K or Q (Lefranc et al, 2001).

Knies et al. (2016) describe that an optimized single-chain TCR (scTCR) inhibits residual TCR mispairing in order to accomplish safe adoptive immunotherapy for bulk endogenous TCRα/β-positive T-cells. Prevention of residual mispairing was achieved by a novel artificial disulfide bond designed between the Vα-domain and the 3'-tail of the linker close to Vβ in a 3-domain scTCR.

Hoffmann et al. (2015) describe a systematic bioinformatics analysis of the structural characteristics of bound and unbound TCR molecules focusing on the Vα/Vβ relative angle and flexibility. Their results demonstrated the importance of this angle for signaling, as several distinct Vα/Vβ-angle based structural clusters could be observed and larger angle flexibilities exist for unbound TCRs than for bound TCRs. A unique center of rotation was identified and the core region around this point is situated at the center between the Vα and Vβ domains, very close to the positions 44 of both Vα and Vβ.

Substitutions in the context of the present invention can be generated with standard methods of protein mutagenesis, like, e.g., site-directed mutagenesis or random mutagenesis of the encoding DNA or cDNA, or genome editing technologies, like CRISPR Cas, TALEN, ZFN, Argonaute (NgAgo) or CRISPR Cpf1. Further, such substitution can be carried out by simply synthesizing the encoding gene, cDNA or mRNA. Nowadays, service providers offer the synthesis of a nucleic acid of a given sequence.

Methods of random mutagenesis or site directed mutagenesis leading to site-specific amino acid substitutions are well known to the skilled person, and are for example disclosed in Labrou et al. (2010) and Trehan et al. (2016).

Methods of genome editing to modify a given amino acid sequence are well known to the skilled person (e.g., CRISPR Cas, TALEN, ZFN, Argonaute (NgAgo) or CRISPR Cpf1), and are for example disclosed in Maeder & Gersbach (2016). Methods of synthesizing genes are well known to the skilled person, and are for example disclosed in Hughes et al. (2011). The disclosure of these references shall be deemed as incorporated herein by reference in their entireties.

As discussed above, some prior art methods suggest the modification of the TCR α and/or β chain by introducing murine constant chains. This approach has the risk of increased immunogenicity due to non-human sequences, which is avoided by the methods and products of the present invention.

Furthermore, the inventors show that the position 44 substitution can have a moderate impact on the binding to the target peptide (i.e., the affinity to the target antigen/MHC complex), which seems due to the fact that, in the tertiary structure of the α and β variable domains, Q44 is maximally distal from the region that is formed by the CDRs.

According to one embodiment, the modified α chain and β chain do not have any substitutions in their constant domains, and/or in their transmembrane domains, as compared to the respective unmodified receptors as identified and/or isolated. Because the constant domain contains a large and highly conserved interface between TCR α and β chain, the impact of even slight modifications would be difficult to circumvent, in terms of pairing behavior, stability and immunogenicity, compared to the replacement of positions in the variable domain.

According to one embodiment, an α chain with position 44 substitution preferably pairs with a T cell receptor (TCR) β chain of which position 44 in the variable domain is substituted by a suitable amino acid. Likewise, in another embodiment, a β chain with position 44 substitution preferably pairs with a T cell receptor (TCR) α chain in the variable domain of which position 44 is substituted by a suitable amino acid.

Hence, in a T-cell that has been modified to express a second, heterologous or transgenic TCR bearing the claimed substitutions, mispairing between a transgenic α chain and an endogenous β chain, or vice versa, is reduced or even avoided.

In such way, an increased abundance of correctly paired transgenic TCRα/β heterodimers can be achieved, which improves the overall avidity of the modified T-cells and avoids adverse reactions, like the induction of graft—versus—host disease (Bendle et al, 2009).

According to one embodiment of said recombinant T cell receptor (TCR) heterodimer, in at least the α or β chain, the amino acid as present at position 44 in the variable domain is substituted by one amino acid selected from the group consisting of Q, R, D, E, K, L, W, and V.

According to one further embodiment, the α chain has a variable domain sequence comprising at least the framework regions of a sequence sharing (having) at least 95% sequence identity with SEQ ID NO 1 or 3, wherein Q, or any other amino acid occurring at position 44 in the variable domain thereof is substituted by another suitable amino acid as disclosed herein, or the β chain has a variable domain sequence comprising the framework regions of a sequence sharing (having) at least 95% sequence identity with SEQ ID NO 2 or 4, wherein Q, or any other amino acid occurring at position 44 in the variable domain is substituted by another suitable amino acid as disclosed herein.

Preferably, said α or β chains have a variable domain sequence comprising at least the framework regions of a sequence sharing (having) at least 96%, more preferably 97%, even more preferably at least 98%, even more preferably at least 99% or, most preferably 100% sequence identity with SEQ ID NO: 1 or 3, or SEQ ID NO: 2 or 4, respectively.

SEQ ID NO: 1 shows the amino acid sequence of the TCR α chain variable domain of TCR R7P1D5 (also known as TRAV5, Lefranc et al. 2001). SEQ ID NO: 2 shows the amino acid sequence of the TCR β chain variable domain of R7P1D5 (also known as TRBV12-4, Lefranc et al. 2001). R7P1D5 is disclosed in U.S. provisional application 62/308, 944, the content of which is herein incorporated by reference. R7P1D5 binds to the peptide called "MAG-003" when bound to the MHC. e.g., of an antigen presenting cell. MAG-003 comprises the amino acid sequence according to the following general formula I (SEQ ID NO: 17):

wherein $X_1$ is selected from the amino acids K and Y, $X_2$ is selected from the amino acids V, L and A, and $X_3$ is selected from V, L, A, and I.

SEQ ID NO: 3 shows the amino acid sequence of the TCR α chain variable domain TRAV 8-6 (Lefranc et al. 2001). SEQ ID NO: 4 shows the amino acid sequence of the TCR β chain variable domain TRBV 6-5 (Lefranc et al. 2001).

Note that in FIGS. 1 and 3, the sequences are shown with the IMGT numbering, which deviates from the naïve numbering of the respective sequences in the sequence listing. The wavy underlines in FIG. 3 indicate blanks which are considered in the IMGT numbering, although they are not occupied by amino acid residues. It is to be understood that Q44 refers to the IMGT numbering as shown in FIGS. 1 and 3, not to the numbering as derivable from the attached sequence listing.

R7P1 D5, which has an α and β chain (TRAV5 and TRBV12-4), and TRAV 8-6 and TRBV 6-5, are only four examples of TCR variable domains that can be used in the context of the present invention. Other TRAV and TRBV subgroups are disclosed on the IGMT website. Note that the TRAV and TRBV can adopt specificity for different target epitope/MHC complexes by suitable adaptation of the CDR sequences, in particular.

Note also that the above mentioned sequences are shown without signal sequences, and that sometimes, the sequence databases show slightly deviating sequences. In the Uniprot database, for example, TRAV8-6 lacks the N-terminal A shown in SEQ ID NO: 3 as well as in FIG. 1, while TRBV6-5 lacks the N-terminal N, and A shown in SEQ ID NO: 4, as well as in FIG. 1.

According to another embodiment of the recombinant T cell receptor (TCR) heterodimer of the invention, the TCR includes one of the preferred substitution pairs selected from the following lists:

αQ44D/βQ44R;   αQ44R/βQ44D;   αQ44E/βQ44K; αQ44K/βQ44E; αQ44D/βQ44K;
αQ44K/βQ44D;   αQ44E/βQ44R;   αQ44R/βQ44E; αQ44L/βQ44W; αQ44W/βQ44L;
αQ44V/βQ44W; and αQ44W/βQ44V;
αW44D/βQ44R;   αW44R/βQ44D;   αW44E/βQ44K; αW44K/βQ44E;   αW44D/βQ44K;   αW44K/βQ44D; αW44E/βQ44R; αW44R/βQ44E; αW44L/βQ44W; αW44/βQ44L; αW44V/βQ44W; and αW44/βQ44V;

αH44D/βQ44R;   αH44R/βQ44D;   αH44E/βQ44K; αH44K/βQ44E; αH44D/βQ44K;
αH44K/βQ44D;   αH44E/βQ44R;   αH44R/βQ44E; αH44L/βQ44W; αH44W/βQ44L;
αH44V/βQ44W; and αH44W/βQ44V;
αK44D/βQ44R; αK44R/βQ44D; αK44E/βQ44K; αK44/βQ44E; αK44D/βQ44K;
αK44/βQ44D; αK44E/βQ44R; αK44R/βQ44E; αK44L/βQ44W; αK44W/βQ44L;
αK44V/βQ44W; and αK44W/βQ44V;
αE44D/βQ44R; αE44R/βQ44D; αE44/βQ44K; αE44K/βQ44E; αE44D/βQ44K;
αE44K/βQ44D; αE44/βQ44R; αE44R/βQ44E; αE44L/βQ44W; αE44W/βQ44L;
αE44V/βQ44W; and αE44W/βQ44V;
αQ44D/βR44; αQ44R/βR44D; αQ44E/βR44K; αQ44K/βR44E; αQ44D/βR44K;
αQ44K/βR44D; αQ44E/βR44; αQ44R/βR44E; αQ44L/βR44W; αQ44W/βR44L;
αQ44V/βR44W; and αQ44W/βR44V;
αW44D/βR44;   αW44R/βR44D;   αW44E/βR44K; αW44K/βR44E; αW44D/βR44K;
αW44K/βR44D;   αW44E/βR44;   αW44R/βR44E; αW44L/βR44W; αW44/βR44L;
αW44V/βR44W; and αW44/βR44V;
αH44D/βR44; αH44R/βR44D; αH44E/βR44K; αH44K/βR44E; αH44D/βR44K;
αH44K/βR44D; αH44E/βR44; αH44R/βR44E; αH44L/βR44W; αH44W/βR44L;
αH44V/βR44W; and αH44W/βR44V;
αK44D/βR44; αK44R/βR44D; αK44E/βR44K; αK44/βR44E; αK44D/βR44K;
αK44/βR44D; αK44E/βR44; αK44R/βR44E; αK44L/βR44W; αK44W/βR44L;
αK44V/βR44W; and αK44W/βR44V;
αE44D/βR44; αE44R/βR44D; αE44/βR44K; αE44K/βR44E; αE44D/βR44K;
αE44K/βR44D;   αE44R/βR44E;   αE44L/βR44W; αE44W/βR44L; αE44V/βR44W;
and αE44W/βR44V.

In the above, e.g. "αQ44R/βQ44D" shall mean for example that, in the variable domain of the α chain, Q44 is substituted by R, while in the variable domain of the β chain, Q44 is substituted by D.

According to preferred embodiments of said recombinant T cell receptor (TCR) heterodimer, a) the modified α chain pairs preferably with the modified β chain, as compared to a non-modified β chain having Q or any other suitable amino acid at position 44 in the variable domain, and/or b) the modified β chain pairs preferably with the modified α chain, as compared to a non-modified α chain having Q or any other suitable amino acid at position 44 in the variable domain.

According to another aspect of the invention, a nucleic acid molecule encoding for a modified T cell receptor (TCR) α or β chain according to the above description and/or a recombinant T cell receptor (TCR) heterodimer according to the above description is provided. In one embodiment, the nucleic acid molecule further comprises at least one of a promoter operably linked to said one or more encoding nucleic acid molecules, and/or a signal sequence operably linked to said one or more encoding nucleic acid molecules.

The signal sequence encodes for a signal peptide that directs the α or β chain to the cellular surface of the T cells, where it is anchored by means of its transmembrane domain, the α and β chain being displayed on the cells outer surface. Signal sequences for the different α and β chain variable domain subtypes are disclosed in the art.

According to another aspect of the invention, a plasmid or vector comprising at least one of the nucleic acid molecules set forth above is provided.

In one embodiment, said vector is preferably a viral vector, preferably a retroviral vector or lentiviral vector. Methods of transducing α or β T cell receptor (TCR) genes into T cells with viral vectors are for example disclosed in Pogulis and Pease (1998), or Zong et al. (2010). The use of Lentiviral vectors for gene transfer into human T cells is disclosed in Verhoeyen et al. (2009).

In one other embodiment, said vector comprises a transposon, like piggyback or sleeping beauty, which in turn is capable of transferring the respective nucleic acid into the T cell. Methods of using transposons for genetically engineering T cells are for example disclosed in Huang et al. (2008).

In another embodiment, the T cell can be transiently transfected, e.g., by means of introducing one or more RNAs encoding for the α and β chains, e.g., by means of electroporation. Such methods are e.g. disclosed in Kim and Eberwine (2010).

According to another aspect of the invention, a method of preparing a modified T cell is provided, said method comprising the steps of:
obtaining a T cell from a subject, and transducing or transfecting said T cell with one or more nucleic acid molecules according to the present invention, or a plasmid or vector according to the present invention.

In a preferred embodiment, said T cell has been obtained from an HLA allele negative donor. For example, if the modified T cell is meant to detect antigens presented by a HLA-A*02 serotype APC, the source that is meant to be modified is preferably obtained from a HLA-A*02 serotype negative donor. In such manner, cross reactivity of the endogenous TCR with the target antigen/MHC complex is reduced, or even avoided.

Preferably, the modified T cell obtained in such way is suitable for autologous T cell treatment of said subject.

According to another aspect of the invention, a modified T cell bearing a set of nucleic acids encoding for the α and β chains of a recombinant T cell receptor (TCR) heterodimer according to the above description is provided.

In one embodiment, said cell has been prepared by a method according to the above description.

According to another aspect of the invention, the use of a modified T cell according to the above description for the treatment of a patient that is suffering from, at risk of developing, and/or being diagnosed for a neoplastic, inflammatory, infectious or autoimmune disease is provided, which use comprises providing or administering to a patient in need thereof a preparation comprising said modified T cell.

Alternatively, a method of treating a patient that is suffering from, at risk of developing, and/or being diagnosed for a neoplastic, inflammatory, infectious or autoimmune disease, with a modified T cell according to the above description is provided, which method comprises providing or administering to a patient in need thereof a preparation comprising said modified T cell.

It is, in this context, important to understand that the specificity of the respective modified TCR, or of the respective modified T cell, is dependent on CDR sequences in the variable domains of the α and β chains, in order to detect antigens presented by the MHC of an antigen presenting cells.

As described in Løset et al. (2014), T cell receptors for a specific antigen—MHC complex can be obtained by T cell related phage display. In such approach, the Q44 substitutions in the variable domains of α and β chain can either be accomplished in all members of the library that forms the basis for the phage display, or can be introduced afterwards, i.e., once a specific TCR that detects a specific antigen—MHC complex has been found.

According to further aspects of the invention, the use, method, T cell or T cell receptor (TCR) heterodimer according to the above description is provided, wherein the antigen presented by the MHC complex detected by the T cell receptor is selected from a cancer specific tumor associated antigen (TAA) peptide epitopes. These peptides are known in the art, and comprise, as an example, peptide MAG-003 as used in the examples. These peptides can be found in the literature, for example the Epitope Database (www.iedb.org/) or preferred as disclosed in any of WO 2016/177784; WO 2016/170139; WO 2016/156230; WO 2016/156202; WO 2016/146751; WO 2016/102272; WO 2016/107740; WO 2015/193359; WO 2015/169945; WO 2015/063302; WO 2015/018805; WO 2012/069462; WO 2012/079878; WO 2012/038463; WO 2011/151403; WO 2011/128448; WO 2011/113882; WO 2011/113872; WO 2011/113819; WO 2011/073215; WO 2010/037514; WO 2009/138236; WO 2007/028574; WO 2007/028573; WO 2006/114307; WO 2005/116051; WO 2005/076009; WO 2004/085461; WO 03/100432; WO 03/102023; WO 2009/015843; WO 2009/015842; WO 2009/015841; WO 2016/202963; WO 2016/207164; WO 2017/001491; WO 2017/005733; WO 2017/021527; WO 2017/036936; WO 2017/060169; WO 2017/060201; WO 2017/097602; WO 2017/097699; WO 2017/108345; or WO 2017/009400 (all hereby incorporated by reference with regards to the disclosed peptides).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, and/or from studying the drawings, the disclosure, and the appended claims.

It is further to be understood that this invention is not limited to the particular component parts or structural features of the devices or compositions described or process steps of the methods described as such devices and methods may vary. It is also to be understood that the terminology used herein is for purposes of describing particular embodiments only, and is not intended to be limiting. The mere fact that certain measures are recited in mutually different dependent claims does not indicate that a combination of these measures cannot be used to advantage. Any reference signs in the claims should not be construed as limiting the scope. It must be noted that, as used in the specification and the appended claims, the singular forms "a," "an" and "the" include singular and/or plural referents unless the context clearly dictates otherwise. Further, in the claims, the word "comprising" does not exclude other elements or steps. The mere fact that certain measures are recited in mutually different dependent claims does not indicate that a combination of these measures cannot be used to advantage. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

All amino acid sequences disclosed herein are shown from N-terminus to C-terminus; all nucleic acid sequences disclosed herein are shown 5'→3'. For the purposes of the present invention, all references as cited herein are incorporated by reference in their entireties. This refers, particularly, for prior art documents that disclose standard or routine methods. In that case, the incorporation by reference has mainly the purpose to provide sufficient enabling disclosure, and avoid lengthy repetitions.

In the figures and the attached sequence listing,

FIGS. 1A to C show the numbering of amino acid residues in the variable domains of TCR α chain and β chain. Figure taken and modified from Lefranc et al. (2003). The sequences are shown on the example of TRAV8-6 (Gene ID: 28680) (alpha chain) (SEQ ID NO: 3) and TRBV6-5 (Gene ID: 28602) (beta chain) (SEQ ID NO: 4). The numbering of the amino acid residues in the α chain and β chain is according to the IMGT standard (bold), compared to the Kabat numbering. In FIG. 1B, Q44 in the α chain (TRAV) and β chain (TRBV) are marked with a grey underlay. Q44 according to the IMGT numbering is a highly conserved residue in the Framework 2 (FR2) region and shared by about 80% of all TCR genes (Strong et al., 1999), including 1G4 (pdb ID: 2BNR (Chen et al., 2005)); TRAV8-6 (Gene ID: 28680) (a chain) (SEQ ID NO: 3) and TRBV6-5 (Gene ID: 28602) (SEQ ID NO: 4), (β chain) and R7P1D5 (comprising TRAV5 (SEQ ID NO: 1) and TRBV12-4 (SEQ ID NO: 2), Lefranc et al. 2001). Q44 is very often part of the 4 AA motif comprising WYXQ, with X being any amino acid, for example, R, V or K. W41 is even more conserved (>95%) in TCR α and β chains (Strong et al., 1999).

FIG. 2A shows the structural motif of the αQ44/βQ44 from the variable domain of the TCR 1G4 (pdb ID: 2BNR (Chen et al., 2005)). FIG. 2B shows in silico double mutants, based on the crystal structure of the 1G4 TCR. From the wild type αQ44/βQ44 pair, the inventors manually selected and engineered potential pairs that maintain a high level of molecular contacts (polar or apolar), while breaking the sterical and/or charge symmetry. The mutants were created with UCSF Chimera (Pettersen et al., 2004). Throughout the whole figures, the TCR α and β chains are represented in dark blue and cyan ribbons, respectively. The side chains of interest are highlighted in magenta and all heavy atoms are shown.

FIG. 3 shows sequences of TCR variants R7P1 05 a and β chains (TRAV5 and TR8V12-4), detects a peptide called MAG-003 when bound to the MHC; TRAV8-6 (a chain variable domain); and TR8V6-5 (β chain variable domain). The grey underlay marks the approximate positions of CDR1 (SEQ ID NO: 5 for TRAV5, SEQ ID NO: 8 for TRBV12-4, SEQ ID NO: 11 for TRAV8-6, and SEQ ID NO: 14 for TRBV6-5), CDR2 (SEQ ID NO: 6 for TRAV5, SEQ ID NO: 9 for TRBV12-4, SEQ ID NO: 12 for TRAV8-6, and SEQ ID NO: 15 for TRBV6-5) and CDR3 (SEQ ID NO: 7 for TRAV5, SEQ ID NO: 10 for TRBV12-4, SEQ ID NO: 13 for TRAV8-6, and SEQ ID NO: 16 for TRBV6-5), with the framework regions FR1, FR2 and FR3. As can be seen, Q44 is located in FR2. Note that Q44 is conserved in other TCR variants, too, just like in TRAV8-6 and TR8V6-5. As in the latter, Q44 is in R7P105 part of a 4 AA motif comprising WYXQ. Depending on the respective antigen that is targeted, the CDR sequences can of course vary.

Figure 4B:
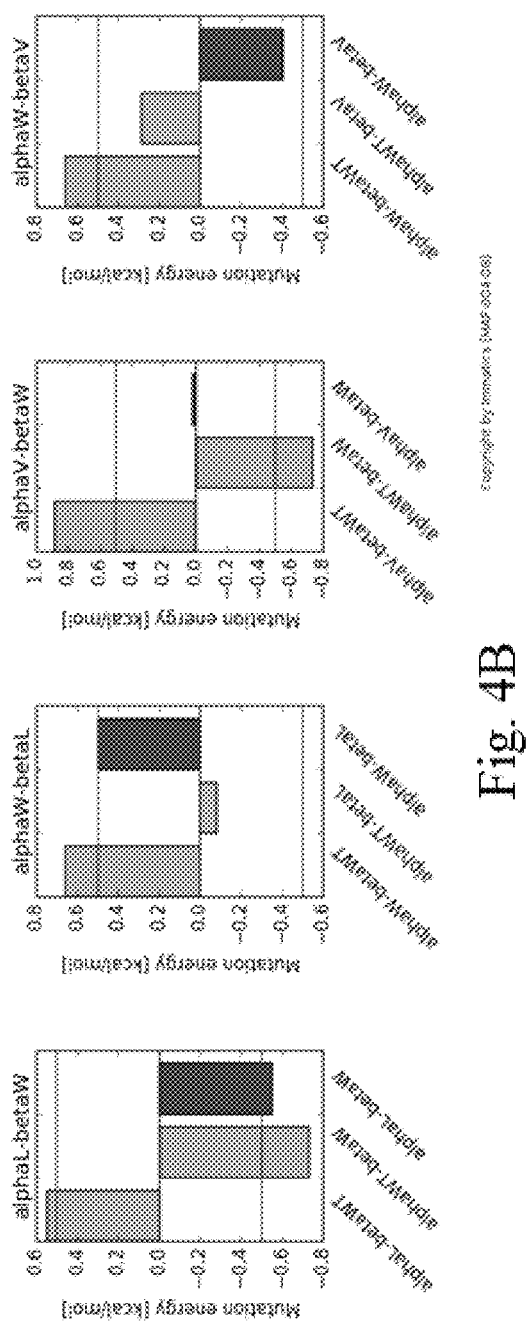

FIG. 4A and FIG. 4B show the computed mutation energies for selected in silico engineered mutants. Double mutations are selected for a resulting shape and/or charge complementarity at the TRAV/TRBV interface. FIG. 4A shows a selection of charged amino acids (D, E, K, R) while FIG. 4B shows a selection of neutral amino acids (W, V, L). For each suggested pair of complementary mutations, the inventors tested the double mutant (green), as well as each individual single mutant (orange) to mimic the pairing of an engineered chain with a wild type chain. Mutation energies higher than 0.5 kcal/mol are considered destabilizing, mutation energies lower than −0.5 kcal/mol are considered stabilizing, mutation energies between −0.5 and 0.5 kcal/mol are considered neutral (in between red lines—software default parameters). The mutations were performed on the variable domain of the 1G4 TCR (Chen et al., 2005) with Discovery Studio (Dassault Systèmes, BIOVIA, 2017) and the mutation energy algorithm described by Spassov and Yan (2013).

Figure 5:
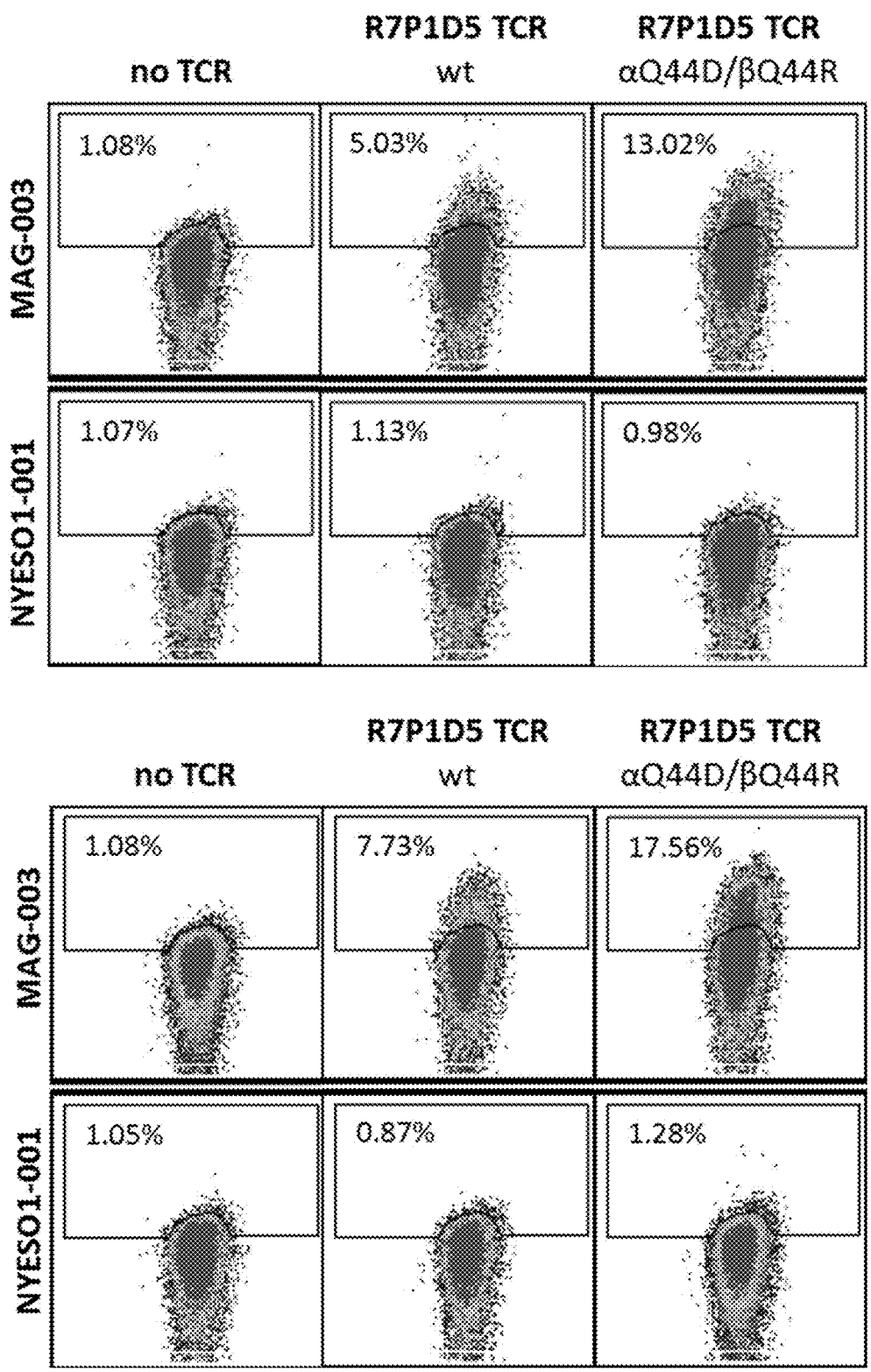

FIG. 5 shows MAG-003 (exemplary peptide): HLA-A*02 tetramer or NYESO1-001(control peptide): HLA-A*02 tetramer staining, respectively, of CD8+ T-cells electroporated with alpha and beta chain RNA of TCR R7P1 D5 wt and mutant variants. R7P1 D5 detects a MAG-003 peptide when bound to the MHC, but does not detect a NYESO1 peptide. Mock-electroporated CD8+ T-cells (no TCR) served as controls. Donors (left panel: donor A, right panel: donor B).

Figure 6:
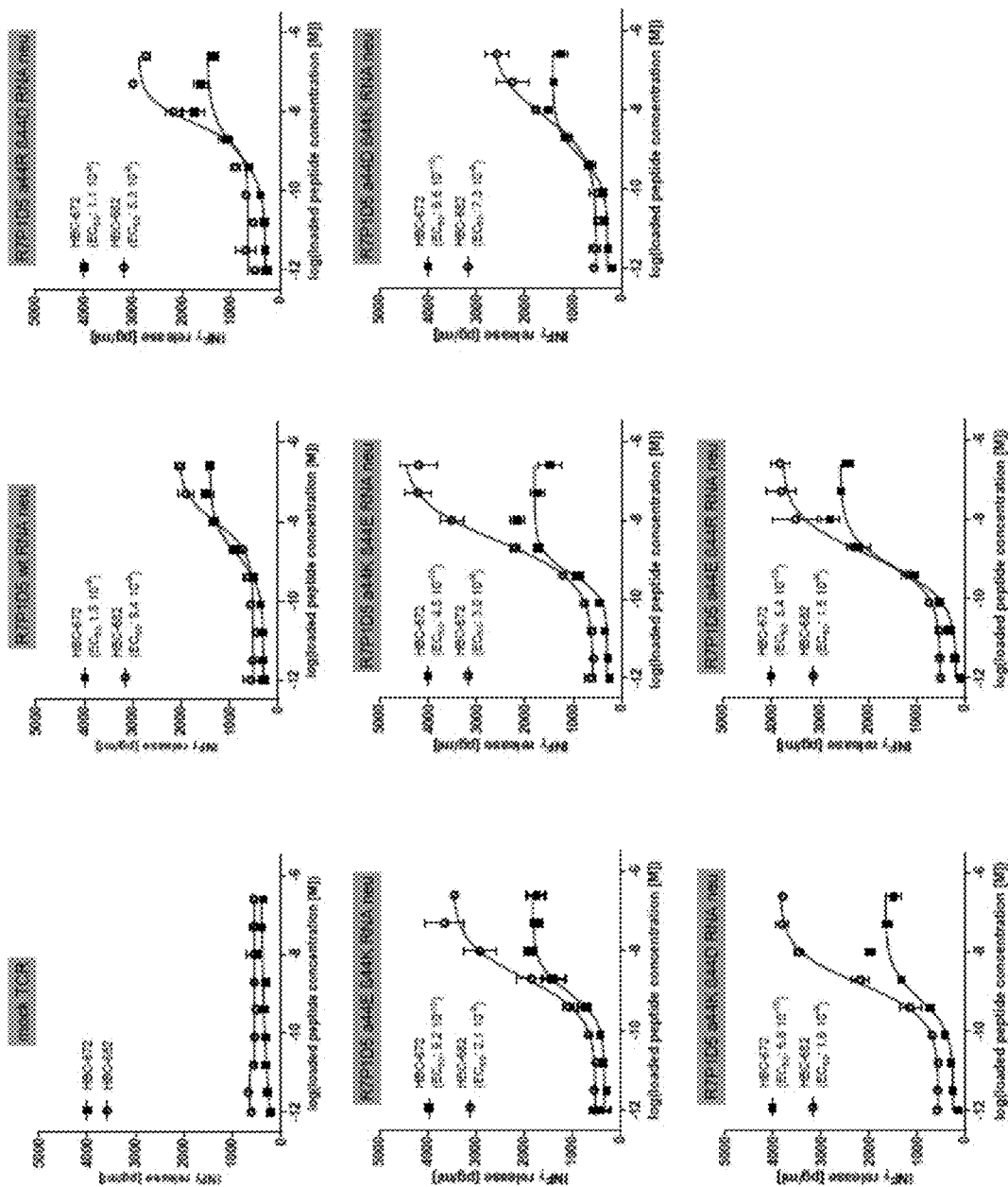

FIG. 6 shows IFN release with MAG-003 as an exemplary peptide in the HLA-A*02 context of CD8+ T-cells that were electroporated with alpha and beta chain RNA of TCR R7P1 D5 wt and mutant variants. All mutant variants (αQ44R/βQ44D, αQ44E/βQ44K, αQ44K/βQ44E, αQ44D/βQ44K, αQ44K/βQ44D, αQ44E/βQ44R) show an improved MAG-003 recognition when compared to unmodified R7P1 D5 wt.

Figure 7:
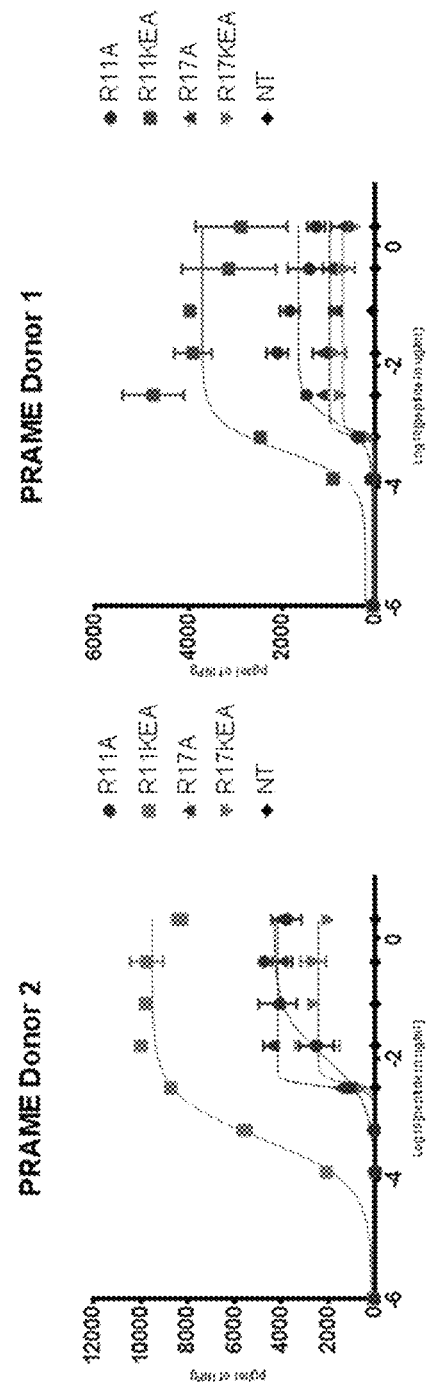

In FIG. 7, PRAME-004 specific TCRs R11A and R17A and their corresponding α44K/β44E mutant variants, respectively were transduced into human T cell via lentiviral transfer. The activity of TCR-transduced T cells was assessed by co-incubation with T2 cells loaded with decreasing concentration of PRAME-004 peptide. Mutant TCR R11KEA shows vastly improved PRAME-004 recognition when compared to unmodified R11 TCR.

Figure 8:
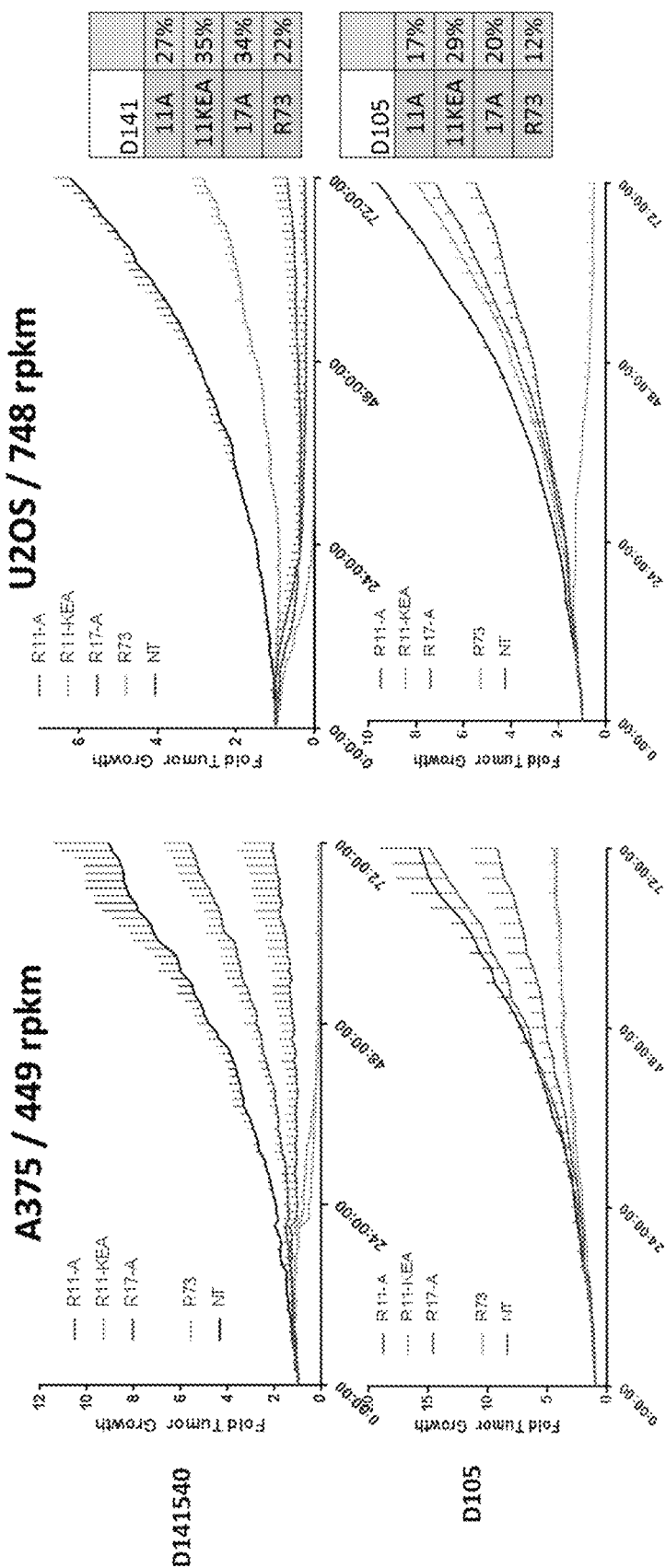

In FIG. 8, PRAME-004 specific TCR R17A and R11A and its corresponding 44K/44E mutant variant (R11KEA) were transduced into human T cell of two donors via lentivirus transfer. Cytotoxicity of transduced T cells against of PRAME-004 expressing tumor cell lines A375 and U2OS was assessed via IncuCyte imaging system. MAG-003 specific TCR was used as control (A375 and U2OS express MAG-003 as well). Mutant TCR R11KEA show increased killing of PRAME-004 positive cell lines when compared to unmodified R11A TCR.

EXAMPLES

Note that the numbering according to the IMGT standard may deviate from the naïve numbering of a given amino acid sequence of a TCR variable domain, in particular due to blanks in the CDR sequences, as can be seen in FIG. 1 A-C.

This applies, e.g., for TRAV8-6 and TRBV6-5, where the wavy underlines show blanks which are considered in the IMGT numbering, although they are not occupied by amino acid residues. These sequences are provided as examples only, and—although preferred—shall not restrict the claims to specific embodiments. This means that the teaching of the present invention is applicable to other TCR α and β chains, or TCR αβ heterodimers, having other sequences, in particular in the variable domain, in particular in the CDRs.

Further, the teaching of the present invention is also applicable to other TCR α and β chains or TCR αβ heterodimers binding to other target antigen/MHC complexes as well, preferably, but not only, when comprising the natural Q44 amino acid, and preferably when they comprise a WYXQ motif. Depending on the respective antigen as targeted, the CDR sequences may vary.

In general, methods of T-Cell Receptor Cloning and Expression have been disclosed in Wälchli et al. (2011). Methods of random mutagenesis or site directed mutagenesis leading to site-specific amino acid substitutions are well known to the skilled person, and are for example disclosed in Labrou (2010) and Trehan et al. (2016).

Methods of genome editing to modify a given amino acid sequence are well known to the skilled person (e.g., CRISPR Cas, TALEN, ZFN, Argonaute (NgAgo) or CRISPR Cpf1), and are for example disclosed in Maeder and Gersbach (2016). Methods of synthesizing genes are well known to the skilled person, and are for example disclosed in Hughes et al. (2011). The disclosure of these references is incorporated by reference in their entireties.

In Silico Methods

By visually inspecting the variable domain of the 1G4 TCR (pdb ID: 2BNR (Chen et al., 2005)), the inventors manually selected pairs of mutations for the α44/β44 motif, that would potentially maintain a high level of molecular contacts (polar or apolar), while breaking the steric and/or charge symmetry. Mutation pairs were selected such that (i) the total charge of the pair was zero, (ii) the two amino acids would potentially show a good shape complementarity and/or form hydrogen bond and/or salt bridges, and (iii) the two amino acids would have a different molecular weight (i.e. one large amino acid and one small amino acid). The Discovery Studio software (Dassault Systèmes, BIOVIA, 2017) was used to investigate further the effect of the engineered positions on the αβ pairing of the TCR. Mutation energies were computed by using the algorithm described by Spassov et al. (Spassov and Yan, 2013) to perform in silico design of antibodies. Mutation energies were expected reflect the effect of a mutation, compared to the wild type motif αQ44/βQ44. The inventors tested double mutants as well as each single mutant paired to a wild type chain:

in case of double mutants, the mutation energy was expected to be neutral or stabilizing in case of single mutants paired to a wild type chain, the mutation energy was expected to be destabilizing for at least one of the two sides.

Human primary CD8+ T cells were electroporated without RNA (no TCR) or with the same amount of RNA encoding for peptide-specific (MAG-003 as an example, peptide "p286" as disclosed, e.g., by Wu et al. Scandinavian journal of immunology 74:6 2011 December pages 561-7) T cell receptor chains α and β in its wild type form (R7P1 D5 TCR wt) or in a mutant form (R7P1 D5 TCR αQ44D/βQ44R) incorporating a Q44D mutation in the TCR alpha variable domain and a Q44R mutation in the TCR beta variable domain. After overnight cultivation the T cells were analyzed for binding of MAG-003:HLA-A*02 tetramers (FIG. 5, upper row) and binding of unrelated peptide NYESO1-001:HLA-A*02 control tetramers (FIG. 5, lower row)(peptide NYESO-001; Epitope ID 59283 in the Epitope Database as above). The proportion of tetramer positive T cells is show for two individual donors (FIG. 5 left panel: donor A, right panel: donor B).

The TCR R7P1 D5, encoding a tumor specific TCR-alpha and TCR-beta chain, was isolated and amplified from T-cells of a healthy donor. Cells from healthy donors were in vitro stimulated according to a method previously described (Walter et al., 2003) and target-specific cells were single-cell sorted using HLA-A*02 multimers and then used for subsequent TCR isolation. TCR sequences were isolated via 5' RACE by standard methods as described by e.g. Molecular Cloning a laboratory manual fourth edition by Green and Sambrook. The alpha and beta variable regions of TCR R7P1 D5 was sequenced and cloned for further functional characterization. TCR R7P1 D5 is derived from a HLA-A*02 positive donor.

REFERENCES AS CITED

Davis M M, Bjorkman P J T-cell antigen receptor genes and T-cell recognition. (1988). 334(6181), 395-402.

Cole D K et al. Germ line-governed recognition of a cancer epitope by an immunodominant human T-cell receptor. (2009). 284(40), 27281-27289.

Li H et al. Structure-function studies of T-cell receptor-superantigen interactions. (1998). 163, 177-186.

Burrows S R Hard wiring of T cell receptor specificity for the major histocompatibility complex is underpinned by TCR adaptability. (2010). 107(23), 10608-10613.

Roomp K Domingues F S (2011). Predicting interactions between T-cell receptors and MHC-peptide complexes. Mol Immunol 48: 553-562.

Rosenberg S A et al. (1988). Use of tumor-infiltrating lymphocytes and interleukin-2 in the immunotherapy of patients with metastatic melanoma. A preliminary report. N Engl J Med 319: 1676-1680.

Shao H et al. TCR mispairing in genetically modified T cells was detected by fluorescence resonance energy transfer. (2010). 37(8), 3951-3956.

Lefranc M P et al. IMGT unique numbering for immunoglobulin and T cell receptor variable domains and Ig superfamily V-like domains. Dev. Comp. Immunol. (2003) 27, 55-77

Lefranc M P et al. The T cell receptor facts book. (2001)

Bendle G M et al. Preclinical development of T cell receptor gene therapy. Curr. Opin. Immunol. (2009). 21, 209-214

Pogulis R J, Pease L R. A retroviral vector that directs simultaneous expression of α and β T cell receptor genes. Hum Gene Ther. (1998) Oct. 10; 9(15): 2299-304.

Zhong S et al. Retroviral Transduction of T-cell Receptors in Mouse T-cells J Vis Exp. (2010); (44): 2307

Wälchli S et al. A Practical Approach to T-Cell Receptor Cloning and Expression. PLOS ONE (2011) 6(11): e27930

O'Shea E K et al. Peptide "Velcro": design of a heterodimeric coiled coil. (1993). 3(10), 658-667.

Chang H C et al. A general method for facilitating heterodimeric pairing between two proteins: application to expression of alpha and beta T-cell receptor extracellular segments. (1994). 91(24), 11408-11412.

Varriale S et al. An evolutionary conserved motif is responsible for immunoglobulin heavy chain packing in the B cell membrane. (2010).

Govers C et al. T cell receptor gene therapy: strategies for optimizing transgenic TCR pairing. Trends Mol Med. (2010) February; 16(2):77-87

Løset G A et al., Phage Display Engineered T Cell Receptors as Tools for the Study of Tumor Peptide-MHC Interactions. Front Oncol (2014); 4: 378.

Hughes R A et al. Gene synthesis: methods and applications. Methods Enzymol. (2011); 498: 277-309

Labrou N E. Random mutagenesis methods for in vitro directed enzyme evolution. Curr Protein Pept Sci. (2010) February; 11(1):91-100.

Trehan A et al. REPLACR-mutagenesis, a one-step method for site-direc Scientific Reports (2016) 6, Article number: 19121

Maeder M L & Gersbach C A. Genome-editing Technologies for Gene and Cell Therapy. Molecular Therapy (2016); 24 3, 430-446.

Verhoeyen E et al. Lentiviral vector gene transfer into human T cells. Methods Mol Biol. 2009; 506:97-114

Huang X et al. Sleeping Beauty Transposon-mediated Engineering of Human Primary T Cells for Therapy of CD19+ Lymphoid Malignancies. Molecular Therapy (2008); 16 3, 580-589.

Kim T K & Eberwine J H. Mammalian cell transfection: the present and the future. Anal Bioanal Chem. 2010 August; 397(8): 3173-3178.

Chen, J L et al. (2005). Structural and kinetic basis for heightened immunogenicity of T cell vaccines. The Journal of Experimental Medicine, 201(8), 1243-1255.

Pettersen E F et al. (2004). UCSF Chimera—a visualization system for exploratory research and analysis. Journal of Computational Chemistry, 25(13), 1605-1612.

Spassov V Z & Yan L (2013). pH-selective mutagenesis of protein-protein interfaces: in silico design of therapeutic antibodies with prolonged half-life. Proteins: Structure, Function, and Bioinformatics, 81(4), 704-714.

Cohen C J et al. Enhanced antitumor activity of murine-human hybrid T-cell receptor (TCR) in human lymphocytes is associated with improved pairing and TCR/CD3 stability. Cancer Res. 2006 Sep. 1; 66(17):8878-86.

Cohen C J et al. Enhanced antitumor activity of T cells engineered to express T-cell receptors with a second disulfide bond. Cancer Res. 2007 Apr. 15; 67(8):3898-903.

Voss R H et al. Molecular design of the Calphabeta interface favors specific pairing of introduced TCRalphabeta in human T cells. J Immunol. 2008 Jan. 1; 180(1):391-401.

Walter et al. (2003) J Immunol., November 15; 171(10): 4974-8.

Knies et al. An optimized single chain TCR scaffold relying on the assembly with the native CD3-complex prevents residual mispairing with endogenous TCRs in human T-cells. Oncotarget. 2016 Apr. 19; 7(16): 21199-21221.

Thomas Hoffmann et al. Quantitative Analysis of the Association Angle between T-cell Receptor Vα/Vβ Domains Reveals Important Features for Epitope Recognition. PLOS, Jul. 17, 2015, dx.doi.org/10.1371/journal.pcbi.1004244

The invention claimed is:

1. A modified T cell receptor (TCR), wherein said TCR comprises an α chain and a β chain, wherein the amino acid at position 44 according to the IMGT numbering comprises an amino acid substitution in a non-modified chain selecting from αQ44R/βQ44D, αQ44D/βQ44K, and αQ44K/βQ44D.

2. A recombinant T cell receptor (TCR) heterodimer comprising a modified α chain and/or a modified β chain, or fragments thereof according to claim 1, wherein said TCR maintains the ability to bind to an antigen-WIC complex.

3. The modified TCR of claim 1, wherein said modification of the α and β chain is αQ44R/βQ44D.

4. The modified TCR of claim 1, wherein said modification of the α and β chain is αQ44D/βQ44K.

5. The modified TCR of claim 1, wherein said modification of the α and β chain is αQ44K/βQ44D.

* * * * *

SEQUENCE LISTING

```
<160> NUMBER OF SEQ ID NOS: 17

<210> SEQ ID NO 1
<211> LENGTH: 92
<212> TYPE: PRT
<213> ORGANISM: Artificial
<220> FEATURE:
<223> OTHER INFORMATION: TCR alpha chain variable domain of R7P1D5
      (TRAV5)

<400> SEQUENCE: 1

Gly Glu Asp Val Glu Gln Ser Leu Phe Leu Ser Val Arg Glu Gly Asp
1               5                   10                  15

Ser Ser Val Ile Asn Cys Thr Tyr Thr Asp Ser Ser Ser Thr Tyr Leu
            20                  25                  30

Tyr Trp Tyr Lys Gln Glu Pro Gly Ala Gly Leu Gln Leu Leu Thr Tyr
        35                  40                  45

Ile Phe Ser Ile Asn Met Asp Met Lys Gln Asp Gln Arg Leu Thr Val
    50                  55                  60

Leu Leu Asn Lys Lys Asp Lys His Leu Ser Leu Arg Ile Ala Asp Thr
65                  70                  75                  80

Gln Thr Gly Asp Ser Ala Ile Tyr Phe Cys Ala Glu
                85                  90

<210> SEQ ID NO 2
<211> LENGTH: 94
<212> TYPE: PRT
<213> ORGANISM: Artificial
<220> FEATURE:
<223> OTHER INFORMATION: TCR beta chain variable domain of R7P1D5
      (TRBV12-4)

<400> SEQUENCE: 2
```

-continued

```
Asp Ala Gly Val Ile Gln Ser Pro Arg His Glu Val Thr Glu Met Gly
1               5                  10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser
                85                  90
```

<210> SEQ ID NO 3
<211> LENGTH: 95
<212> TYPE: PRT
<213> ORGANISM: Artificial
<220> FEATURE:
<223> OTHER INFORMATION: TCR alpha chain variable domain of TRAV 8-6

<400> SEQUENCE: 3

```
Ala Gln Ser Val Thr Gln Leu Asp Ser Gln Val Pro Val Phe Glu Glu
1               5                  10                  15

Ala Pro Val Glu Leu Arg Cys Asn Tyr Ser Ser Ser Val Ser Val Tyr
            20                  25                  30

Leu Phe Trp Tyr Val Gln Tyr Pro Asn Gln Gly Leu Gln Leu Leu Leu
        35                  40                  45

Lys Tyr Leu Ser Gly Val Ser Thr Leu Val Glu Ser Ile Asn Gly Phe
    50                  55                  60

Glu Ala Glu Phe Asn Lys Ser Gln Thr Ser Phe His Leu Arg Lys Pro
65                  70                  75                  80

Ser Val His Ile Ser Asp Thr Ala Glu Tyr Phe Cys Ala Val Ser
                85                  90                  95
```

<210> SEQ ID NO 4
<211> LENGTH: 95
<212> TYPE: PRT
<213> ORGANISM: Artificial
<220> FEATURE:
<223> OTHER INFORMATION: TCR beta chain variable domain of TRBV 6-5

<400> SEQUENCE: 4

```
Asn Ala Gly Val Thr Gln Thr Pro Lys Phe Gln Val Leu Lys Thr Gly
1               5                  10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr
                85                  90                  95
```

<210> SEQ ID NO 5
<211> LENGTH: 6
<212> TYPE: PRT
<213> ORGANISM: Artificial

```
<220> FEATURE:
<223> OTHER INFORMATION: CDR1 of TRAV 5

<400> SEQUENCE: 5

Asp Ser Ser Ser Thr Tyr
1               5

<210> SEQ ID NO 6
<211> LENGTH: 3
<212> TYPE: PRT
<213> ORGANISM: Artificial
<220> FEATURE:
<223> OTHER INFORMATION: CDR2 of TRAV 5

<400> SEQUENCE: 6

Ile Phe Ser
1

<210> SEQ ID NO 7
<211> LENGTH: 3
<212> TYPE: PRT
<213> ORGANISM: Artificial
<220> FEATURE:
<223> OTHER INFORMATION: CDR3 of TRAV 5

<400> SEQUENCE: 7

Cys Ala Glu
1

<210> SEQ ID NO 8
<211> LENGTH: 5
<212> TYPE: PRT
<213> ORGANISM: Artificial
<220> FEATURE:
<223> OTHER INFORMATION: CDR1 of TRBV 12-4

<400> SEQUENCE: 8

Ser Gly His Asp Tyr
1               5

<210> SEQ ID NO 9
<211> LENGTH: 5
<212> TYPE: PRT
<213> ORGANISM: Artificial
<220> FEATURE:
<223> OTHER INFORMATION: CDR2 of TRBV 12-4

<400> SEQUENCE: 9

Phe Asn Asn Asn Val
1               5

<210> SEQ ID NO 10
<211> LENGTH: 4
<212> TYPE: PRT
<213> ORGANISM: Artificial
<220> FEATURE:
<223> OTHER INFORMATION: CDR3 of TRBV 12-4

<400> SEQUENCE: 10

Phe Cys Ala Ser
1

<210> SEQ ID NO 11
<211> LENGTH: 7
<212> TYPE: PRT
<213> ORGANISM: Artificial
<220> FEATURE:
```

<223> OTHER INFORMATION: CDR1 of TRAV 8-6

<400> SEQUENCE: 11

Ser Ser Ser Val Ser Val Tyr
1               5

<210> SEQ ID NO 12
<211> LENGTH: 4
<212> TYPE: PRT
<213> ORGANISM: Artificial
<220> FEATURE:
<223> OTHER INFORMATION: CDR2 of TRAV 8-6

<400> SEQUENCE: 12

Tyr Leu Ser Gly
1

<210> SEQ ID NO 13
<211> LENGTH: 3
<212> TYPE: PRT
<213> ORGANISM: Artificial
<220> FEATURE:
<223> OTHER INFORMATION: CDR3 of TRAV 8-6

<400> SEQUENCE: 13

Ala Val Ser
1

<210> SEQ ID NO 14
<211> LENGTH: 5
<212> TYPE: PRT
<213> ORGANISM: Artificial
<220> FEATURE:
<223> OTHER INFORMATION: CDR1 of TRBV 6-5

<400> SEQUENCE: 14

Met Asn His Glu Tyr
1               5

<210> SEQ ID NO 15
<211> LENGTH: 5
<212> TYPE: PRT
<213> ORGANISM: Artificial
<220> FEATURE:
<223> OTHER INFORMATION: CDR2 of TRBV 6-5

<400> SEQUENCE: 15

Ser Val Gly Ala Gly
1               5

<210> SEQ ID NO 16
<211> LENGTH: 4
<212> TYPE: PRT
<213> ORGANISM: Artificial
<220> FEATURE:
<223> OTHER INFORMATION: CDR3 of TRBV 6-5

<400> SEQUENCE: 16

Ala Ser Ser Tyr
1

<210> SEQ ID NO 17
<211> LENGTH: 9
<212> TYPE: PRT
<213> ORGANISM: Artificial Sequence
<220> FEATURE:
<223> OTHER INFORMATION: MAG-003

-continued

```
<220> FEATURE:
<221> NAME/KEY: misc_feature
<222> LOCATION: (1)..(1)
<223> OTHER INFORMATION: Lys or Tyr
<220> FEATURE:
<221> NAME/KEY: misc_feature
<222> LOCATION: (2)..(2)
<223> OTHER INFORMATION: Val or Leu or Ala
<220> FEATURE:
<221> NAME/KEY: misc_feature
<222> LOCATION: (9)..(9)
<223> OTHER INFORMATION: Val or Leu or Ala or Ile

<400> SEQUENCE: 17

Xaa Xaa Leu Glu His Val Val Arg Xaa
1               5
```